United States Patent [19]

Enari et al.

[11] Patent Number: 4,902,702

[45] Date of Patent: Feb. 20, 1990

[54] NOVEL AZOLE DERIVATIVE AND AGRICULTURAL/HORTICULTURAL FUNGICIDE CONTAINING SAID DERIVATIVE AS ACTIVE INGREDIENT

[75] Inventors: Hiroyuki Enari; Satoru Kumazawa; Susumu Shimizu; Atsushi Ito; Nobuo Sato; Toshihide Saishoji, all of Iwaki, Japan

[73] Assignee: Kureha Kagaku Kogyo Kabushiki Kaisha, Tokyo, Japan

[21] Appl. No.: 129,629

[22] Filed: Dec. 7, 1987

[30] Foreign Application Priority Data

Dec. 22, 1986 [JP] Japan ................................. 61-305908

[51] Int. Cl.⁴ ................. A01N 43/653; C07D 249/08
[52] U.S. Cl. ...................................... 514/383; 548/262
[58] Field of Search .......................... 514/383; 548/262

[56] References Cited

U.S. PATENT DOCUMENTS 4,503,062  3/1985  Gravestock ......................... 548/262

FOREIGN PATENT DOCUMENTS

A10153797   9/1985  European Pat. Off. .
60-215674  10/1985  Japan .................................. 548/262
62-149667   7/1987  Japan .................................. 548/262

OTHER PUBLICATIONS

Chemical Abstracts, vol. 91, No. 17, pp. 660, Abstract No. 140844g (1979).

*Primary Examiner*—Glennon H. Hollrah
*Assistant Examiner*—Patricia L. Morris
*Attorney, Agent, or Firm*—Nixon & Vanderhye

[57] ABSTRACT

An azole derivative represented by the formula (I):

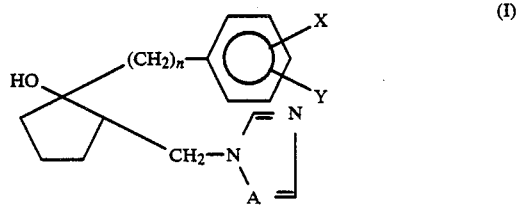

wherein X and Y independently represent a halogen atom, a phenyl group or a hydrogen atom, providing that at least one of X and Y is not a hydrogen atom, n represents an integer of 0, 1 or 2, and A represents a nitrogen atom or CH, and an agricultural/horticultural fungicide comprising the azole derivative as an active ingredient are disclosed.

The azole derivative exhibits an excellent effect in preventing and curing a wide spectrum of plant diseases and possesses low toxicity to mammals.

3 Claims, No Drawings

NOVEL AZOLE DERIVATIVE AND AGRICULTURAL/HORTICULTURAL FUNGICIDE CONTAINING SAID DERIVATIVE AS ACTIVE INGREDIENT

BACKGROUND OF THE INVENTION

The present invention relates to an azole derivative useful as an active ingredient for preventing and curing plant diseases, a process for the production of the azole derivative, and an agricultural/horticultural fungicide containing the azole derivative as an active ingredient thereof.

Numerous azole derivatives have been heretofore proposed for use as an active ingredient of agricultural/horticultural fungicides. The azole derivatives disclosed in Japanese Patent Application Laid-Open (KOKAI) No. 215,674 (1985) have an azolylmethyl group and a phenyl group bonded to the same carbon atom as shown by the following formula:

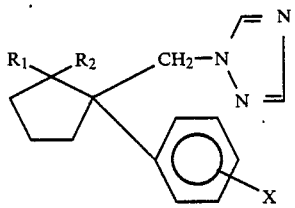

wherein $R_1$ and $R_2$ independently represent a hydrogen atom, a hydroxyl group or an alkyl group having 1 to 6 carbon atoms and X represents a hydrogen atom or a halogen atom.

Japanese Patent Application Laid-Open (KOKAI) No. 149,667 (1987) discloses compounds represented by the following formula:

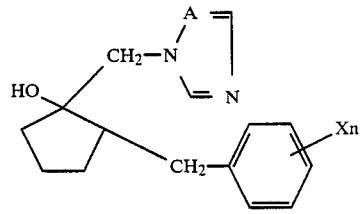

wherein Xs independently represent a halogen atom, an alkyl group, a haloalkyl group, a phenyl group, a cyano group, or a nitro group, n represents an integer in the range of 0 to 5, and A represents a nitrogen atom or CH.

The present inventors, with a view to developing an agricultural/horticultural fungicide possessing low toxicity to mammals, warranting safe handling, and exhibiting a highly satisfactory effect in preventing and curing a wide spectrum of plant diseases, have synthesized many azole derivatives and tested the practicability thereof as a fungicide. The present inventors have consequently found that the azole derivatives of a configuration having an azolylmethyl group and a benzyl group, a phenyl group, or a phenethyl group respectively bonded to adjacent carbon atoms in a cyclopentane ring are useful as an active ingredient of agricultural/horticultural fungicides possessing the aforementioned characteristics. The present invention has been accomplished based on this finding.

SUMMARY OF THE INVENTION

In a first aspect of the present invention, there is provided an azole derivative represented by the formula (I):

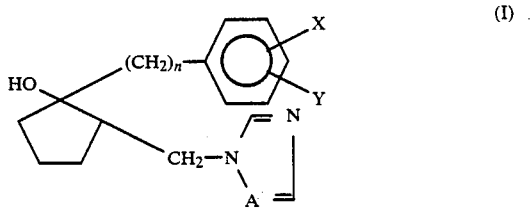

wherein X and Y independently represent a halogen atom, a phenyl group, or a hydrogen atom, providing that at least one of X and Y is not a hydrogen atom, n represents an integer of 0, 1 or 2, and A represents a nitrogen atom or In a second aspect of the present invention, there is provided a process for the production of an azole derivative represented by the formula (I):

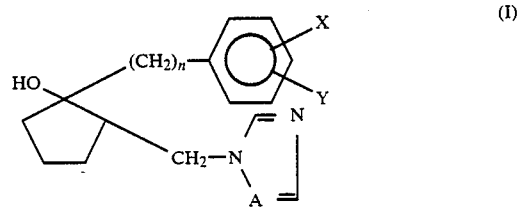

wherein A, X, Y and n have the same meanings as defined above, which comprises reacting a cyclopentanone derivative represented by the following formula (II):

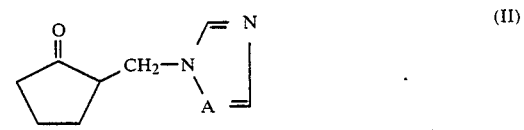

wherein A has the same meaning as defined above, with a Grignard reagent represented by the following formula (III):

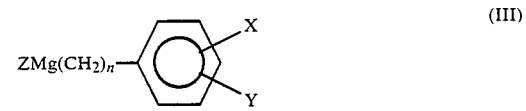

wherein X, Y and n have the same meanings as defined above and Z represents a halogen atom.

In a third aspect of the present invention, there is provided a process for the production of an azole derivative represented by the following formula (I):

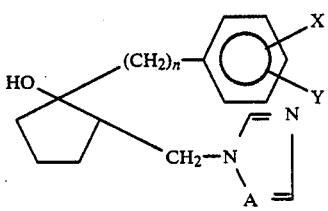

(I)

wherein A, X, Y and n have the same meanings as defined above, which comprises hydrolyzing the ketal group in a cyclopentanone derivative represented by the following formula (IV):

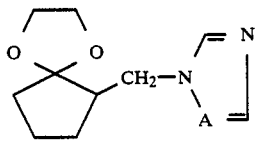

(IV)

wherein A has the same meaning as defined above, thereby obtaining a cyclopentanone derivative represented by the following formula (II):

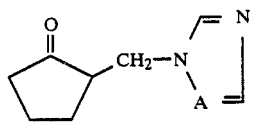

(II)

wherein A has the same meaning as defined above, and reacting said cyclopentanone derivative with a Grignard reagent represented by the following formula (III):

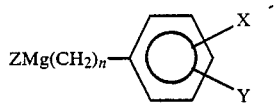

(III)

wherein X, Y, Z and n have the same meanings as defined above.

In a fourth aspect of the present invention, there is provided a cyclopentanone derivative represented by the following formula (II):

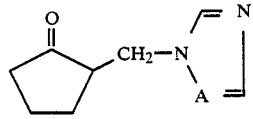

(II)

wherein A has the same meaning as defined above.

In a fifth aspect of the present invention, there is provided a cyclopentanone derivative represented by the following formula (IV):

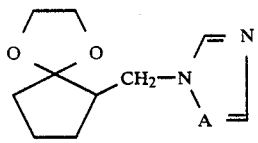

(IV)

wherein A has the same meaning as defined above.

In the sixth aspect of the present invention, there is provided an agricultural/horticultural fungicide comprising as an active ingredient a fungicidally effective amount of an azole derivative represented by the following formula (I):

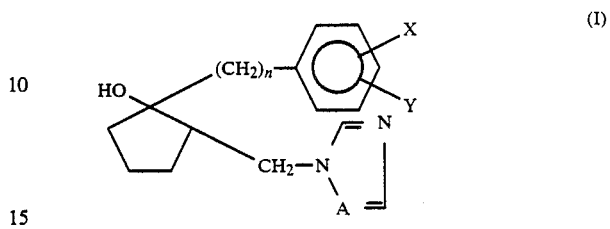

(I)

wherein A, X, Y and n have the same meanings as defined above.

In a seventh aspect of the present invention, there is provided a method for preventing and curing plant diseases which comprises applying a fungicidally effective amount of an azole derivative represented by the following formula (I):

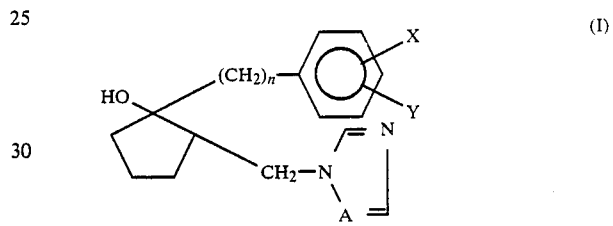

(I)

wherein A, X, Y and n have the same meanings as defined above, to plants.

BRIEF EXPLANATION OF THE DRAWINGS

FIG. 1 to FIG. 7 are infrared absorption spectra of the compounds No. 1 to No. 7 according to the present invention listed in Table 1.

FIG. 8 and FIG. 9 are infrared absorption spectra of cyclopentanone derivatives represented by the formula (II) (FIG. 8 representing a compound having a CH group as the substituent A in the formula (II) and FIG. 9 a compound having a N atom as the substituent A in the formula (II)).

FIG. 10 and FIG. 11 are infrared absorption spectra of ketals of cyclopentanone derivatives represented by the formula (IV) (FIG. 10 representing a compound having a CH group as the substituent A in the formula (IV) and FIG. 11 a compound having a N atom as the substituent A in the formula (IV)).

DETAILED DESCRIPTION OF THE INVENTION

The present invention relates to an azole derivative useful as an active ingredient of an agricultural/horticultural fungicide, a process for the production of the azole derivative, and an agricultural/horticultural fungicide comprising as an active component the aforementioned azole derivative, exhibiting a highly desirable effect in preventing and curing a wide spectrum of plant diseases, possessing low toxicity to mammals, and excelling in safety of handling.

The azole derivatives of the present invention are represented by the following formula (I):

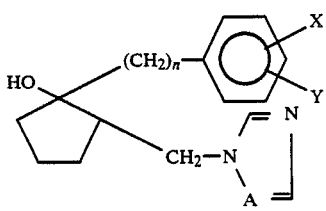

(I)

wherein X and Y independently represent a halogen atom, a phenyl group or a hydrogen atom, providing that at least one of X and Y is not a hydrogen atom, n represents an integer of 0, 1 or 2, and A represents a nitrogen atom or CH.

The azole derivatives represented by the formula (I) are novel compounds not reported yet in literature. The melting points of examples of the compounds according to the present invention are shown in Table 1.

TABLE 1

| Compound No. | Meaning of symbol used in Formula (I) | | | | Melting point (°C.) |
|---|---|---|---|---|---|
| | X | Y | n | A | |
| 1 | 4-Cl | H | 0 | N | Oily state |
| 2 | 4-Cl | H | 1 | N | 127–130 |
| 3 | 4-Cl | H | 1 | CH | 152–153 |
| 4 | 4-Cl | 2-Cl | 1 | N | 108–110 |
| 5 | 4-Ph | H | 1 | N | 153–154 |
| 6 | 4-F | 2-F | 1 | N | Oily state |
| 7 | 4-Cl | H | 2 | N | Oily state |

The infrared absorption spectra of the compounds cited exemplarily in Table 1 are shown in FIGS. 1 to 7 respectively.

The azole derivative according to the present invention is produced by the following method.

The azole derivative represented by the formula (I) is obtained by reacting a cyclopentanone derivative represented by the following formula (II):

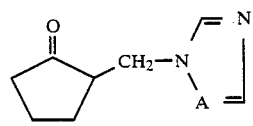

(II)

wherein A stands for a nitrogen atom or CH, with a Grignard reagent represented by the following formula (III):

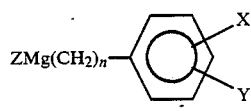

(III)

wherein X and Y independently represent a halogen atom, a phenyl group or a hydrogen atom, providing that at least one of X and Y is not a hydrogen atom, n represents an integer of 0, 1 or 2, and z represents a halogen atom, in the presence of a diluent.

The cyclopentanone derivative of the formula (II) which is used as the starting material herein is a novel compound not reported yet in literature and is obtained by reacting a known ketone represented by the following formula (V):

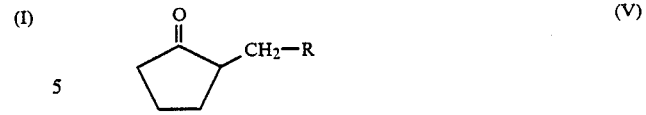

(V)

wherein R represents an elimination group such as a halogen atom, a methanesulfonyloxy group and a paratoluenesulfonyloxy group (for example, the compound

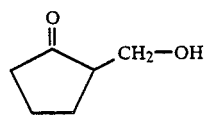

is disclosed in Bull. Chem. Soc. Japan, 1975, Vol. 48, No. 9, 2579–2583), with 1,2,4-triazole or imidazole represented by the following formula (VI):

(VI)

wherein M represents a hydrogen atom or an alkali metal and A represents a nitrogen atom or CH, in the presence of a diluent.

The cyclopentanone derivative represented by the formula (II) can be also obtained by hydrolyzing, under an acidic condition, a ketal of cyclopentanone derivative represented by the following formula (IV):

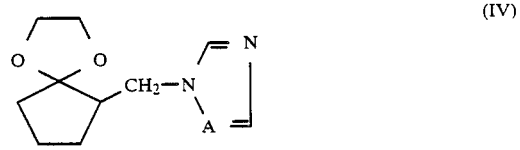

(IV)

wherein A represents a nitrogen atom or CH, which is obtained by reacting a known ketal represented by the following formula (VII):

(VII)

wherein R represents an elimination group such as a halogen atom, a methanesulfonyloxy group and a paratoluenesulfonyloxy group (for example, the compound

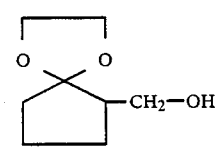

is disclosed in J. Chem. Soc. Perkin Trans. 1, 1978, No. 3, 209–214), with 1,2,4-triazole or imidazole represented by the aforementioned formula (VI) in the presence of a diluent.

As examples of the diluent which is used in the process for the production of the compound represented by the formula (I), there can be cited ethers such as diethyl ether, diisopropyl ether and tetrahydrofuran and aromatic hydrocarbons containing ethers such as benzene and toluene containing ethers. Among the diluents cited above, ethers are particularly preferable.

The process of production according to the present invention can be worked out, for example, by dissolving a Grignard reagent represented by the formula (III) in a diluent described above and adding to the resultant solution a cyclopentanone derivative represented by the formula (II) preferably in an amount in the range of 0.3 to 1.0 equivalent to the Grignard reagent, or conversely by dissolving the cyclopentanone derivative in the diluent and adding to the resultant solution a solution of the Grignard reagent in the diluent.

Though the reaction can be carried out at any desired temperature between the freezing point and the boiling point of the diluent used as a solvent, it is practically preferable to be carried out at a temperature in the range of 0° to 80° C. The reaction time is preferably in the range of 0.5 to 3.0 hours. The reaction is preferably carried out under stirring.

After the reaction described above is completed, the compound represented by the formula (I) is obtained by pouring the reaction mixture resulting from the reaction into ice water, extracting the resultant mixture with an organic solvent such as ethyl acetate, chloroform and benzene, separating an organic layer from the mixture, washing the organic layer with water and drying the washed organic layer, evaporating the dry organic layer under a reduced pressure, and purifying the resultant residue. This purification can be effected by means of recrystallization or silica gel column chromatography, for example.

As examples of the diluent which is used in producing the cyclopentanone derivative represented by the formula (II) from the compound of the formula (V) and the compound of the formula (VI), there can be cited hydrocarbons such as benzene, toluene, xylene and hexane; halogenated hydrocarbons such as methylene chloride, chloroform and carbon tetrachloride; ethers such as diethyl ether, diisopropyl ether and tetrahydrofuran; and acetonitrile, dimethyl formamide, and dimethyl sulfoxide.

The production of the cyclopentanone derivative represented by the formula (II) is effected, for example, by dissolving a compound represented by the formula (VI) in a diluent described above and adding to the resultant solution a compound represented by the formula (V), either directly or in a state dissolved in the diluent, preferably in an amount in the range of 0.3 to 1.0 equivalent to the compound of (VI), or conversely by dissolving the compound represented by the formula (V) in the diluent and adding to the resultant solution a solution of the compound represented by the formula (VI) in a diluent.

Though the reaction can be carried out at any desired temperature between the freezing point and the boiling point of the diluent used as a solvent, it is practically preferable to be carried out at a temperature in the range of 0° to 80° C. The reaction time is preferably in the range of 0.5 to 3.0 hours. The reaction is preferably carried out under stirring.

After the reaction described above is completed, the compound represented by the formula (II) is obtained by pouring the reaction mixture resulting from the reaction into ice water, extracting the resultant mixture with an organic solvent such as ethyl acetate, chloroform and benzene, separating an organic layer from the mixture, washing the organic layer with water, drying the washed organic layer, evaporating the dry organic layer under a reduced pressure, and purifying the resultant residue. This purification can be effected by means of silica gel column chromatography, for example.

As examples of the diluent which is used in producing the cyclopentanone derivative represented by the formula (II) from the compound of the formula (VII) and the compound of the formula (VI), there can be cited hydrocarbons such as benzene, toluene, xylene and hexane; halogenated hydrocarbons such as methylene chloride, chloroform and carbon tetrachloride; ethers such as diethyl ether, diisopropyl ether and tetrahydrofuran; and acetonitrile, dimethyl formamide, and dimethyl sulfoxide.

The production of the compound represented by the formula (II) described above is effected, for example, by dissolving a compound represented by the formula (VI) in a diluent described above and adding to the resultant solution a compound represented by the formula (VII), either directly or in a state dissolved in the diluent, preferably in an amount in the range of 0.3 to 1.0 equivalent to the compound of (VI), or conversely by dissolving the compound of the formula (VII) in the diluent and adding to the resultant solution a solution of the compound represented by the formula (VI) in a diluent.

Though this reaction can be carried out at any desired temperature between the freezing point and the boiling point of the diluent used as a solvent, it is practically preferable to be carried out at a temperature in the range of 0° to 150° C. The reaction time is preferably in the range of 0.5 to 3.0 hours. The reaction is preferably carried out under stirring.

After the reaction described above is completed, the compound represented by the formula (IV) is obtained by pouring the reaction mixture resulting from the reaction into ice water, extracting the resultant mixture with an organic solvent such as ethyl acetate, chloroform and benzene, separating an organic layer from the mixture, washing the organic layer with water, drying the washed organic layer, evaporating the dry organic layer under a reduced pressure, and purifying the resultant residue. This purification can be effected by means of silica gel column chromatography, for example.

As examples of the diluent which is used in producing the cyclopentanone derivative represented by the formula (II) from the compound of the formula (IV), there can be cited hydrocarbons such as benzene, toluene, xylene and hexane; alcohols such as methanol and ethanol; ethers such as diethyl ether, diisopropyl ether and tetrahydrofuran; and acetonitrile, dimethylformamide, and dimethyl sulfoxide. The use of such a diluent as described above is not always required herein.

In the production described above, the reaction is occasionally carried out in the presence of an acid in the presence or absence of the aforementioned diluent. As examples of the acid thus used in the reaction, there can be cited inorganic acids such as hydrochloric acid, hydrobromic acid, hydroiodic acid and sulfuric acid, and organic acids such as acetic acid, tartaric acid and benzoic acid.

The production described above is carried out by adding an acid exemplified above to an intermediate represented by the formula (IV) optionally dissolved in the aforementioned diluent.

Though the reaction can be carried out at a desired temperature in the range of the freezing point and the boiling point of the aforementioned diluent as a solvent or the acid, it is practically preferable to be carried out at a temperature in the range of 0° to 150° C. The reaction time is preferably in the range of 0.5 to 3 hours. This reaction is preferably carried out under stirring.

After the reaction described above is completed, the compound represented by the formula (II) is obtained by pouring the reaction mixture resulting from the reaction into ice water, extracting the resultant mixture with an organic solvent such as ethyl acetate, chloroform and benzene, separating an organic layer from the mixture, washing the organic layer with water, drying the washed organic layer, evaporating the dry organic layer under a reduced pressure, and purifying the resultant residue. This purification can be effected by means of silica gel column chromatography, for example.

Now, the usefulness of the azole derivatives of the present invention represented by the formula (I) as an active ingredient of agricultural/horticultural fungicide will be described below.

The azole derivatives according to the present invention are effective in preventing and curing the broad spectrum of plant diseases such as,

*Pseudoperonospora cubensis* of cucumber, *Pyricularia oryzae* of rice, *Cochliobolus miyabeanus* of rice, *Xanthomonas oryzae* of rice, *Rhizoctonia solani* of rice, *Helminthosporium sigmoideum* of rice, *Gibberella fujikuroi* of rice, *Podosphaera leucotricha* of apple, *Venturia inaequalis* of apple, *Sclerotinia mali* of apple, *Alternaria mali* of apple, *Valsa mali* of apple, *Alternaria kikuchiana* of pear, *Phyllactinia pyri* of pear, *Venturia nashicola* of pear, *Uncinula necator* of grape, *Phakospora ampelopsidis* of grape, *Erysiphe graminis* f. sp. *hordei* of barley, *Rhynchosporium secalis* of barley, *Puccinia graminis* of barley, *Puccinia triformis* of barley, *Puccinia recondita* of wheat, *Septoria tritici* of wheat, *Puccinia triformis* of wheat, *Erysiphe graminis* f. sp. *tritici* of wheat, *Sphaerotheca fuliginea* of melon, *Fusarium oxysporum* of water melon, *Erysiphe cichoracearum* of tomato, *Alternaria solani* of tomato, *Erysiphe cichoracearum* of eggplant, *Sephaerotheca humuli* of strawberry, *Erysiphe cichoracearum* of tobacco, *Alternaria longipes* of tobacco, *Sclerotinia cinerea* of peach, *Fusarium oxysporum* f. *cucumerinum* of cucumber, *Fusarium oxysporum* f. *raphani* of radish, *Colletotrichum lagenarium* of melons, *Cercospora beticola* of beet, *Alternaria solani* of potato, *Septoria glycines* of soybean, *Cercospora kikuchii* of soybean, *Sclerotinia cinerea* of stone-fruits, *Botrytis cinerea* and *Sclerotinia sclerotiorum* of various crops.

The azole derivatives of the present invention shows not merely a preventive effect but also a curative effect on some of the aforementioned plant diseases.

The use of an azole derivative represented by the formula (I) in an agricultural/horticultural fungicide can be attained by formulating the compound, either directly or as mixed with a carrier or a diluent, in the form of dust, wettable powder, granules, emulsion, or solution so as to be advantageously used in an intended application. Of course, the aforementioned effect of the fungicide can be further enhanced by allowing the fungicide to incorporate therein such adjuvants as spreader, emulsifier, wetting agent, and fixing agent, when necessary, in addition to the aforementioned carrier.

Incidentally, the azole derivative according to the present invention contains a 1,2,4-triazole ring or an imidazole ring and, therefore, can be used also in the form of an inorganic acid salt, an organic acid salt, or a metal complex salt.

Further, since the azole derivative according to the present invention possesses a substituted phenylalkyl group and an azolylmethyl group respectively at the 1st position and the 2nd position of a cyclopentane ring, stereoisomers such as geometric isomers and optical isomers exist. The present invention includes all the independent isomers and mixtures of varying isomers in desired ratios. The agricultural/horticultural fungicides according to the present invention, therefore, include those fungicides containing as an active ingredient these isomers either independently or in the form of mixtures.

Now, typical processes adopted for the production of azole derivatives and cyclopentanone derivatives as intermediate therefor and typical agricultural/horticultural fungicides using such azole derivatives as an active ingredient will be explained below for the purpose of demonstrating the effect of the present invention. It should be noted, however, that the present invention is not limited to the working examples below.

EXAMPLE 1

Production of 1-(4-chlorophenyl)-2-(1H-1,2,4-triazol-1-ylmethyl)-cyclopentan-1-ol (Compound No. 1 in Table 1)

A Grignard reagent (4was chlorophenylmagnesium bromide) was prepared by suspending 0.22 g (9.1 mmol) of magnesium powder in 20 ml of anhydrous diethyl ether and after adding 0.1 g of 4-bromo-1-chlorobenzene and a trace amount of $I_2$ thereto, the mixture was refluxed. The Grignard reagent was further subjected to 10 minutes' reflux after slowly adding a solution of 1.64 g (8.6 mmol) of 4-bromo-1-chlorobenzene in 5 ml of anhydrous diethyl ether. The resultant reaction mixture was cooled over an ice-water bath. Then, a solution of 1.0 g (6.0 mmol) of 2-(1H-1,2,4-triazol -1-ylmethyl)-cyclopentanone in 5 ml of anhydrous diethyl ether was added dropwise to the cooled reaction mixture. The mixture consequently formed was removed from the ice-water bath and stirred at room temperature for 30 minutes. The resultant solution, after adding 1N HCl thereto, was extracted with ethyl acetate. The ethyl acetate layer was separated, washed with saturated sodium chloride solution, and dried over anhydrous sodium sulfate. The dried solution was then evaporated under a reduced pressure. The residue of the evaporation was purified by silica gel column chromatography (eluate - 20:1 mixture of chloroform and methanol). Consequently, 150 mg of an oily compound No. 1 was obtained (9% yield).

This compound No. 1 was found by test to possess the following properties. The NMR spectrum was measured with TMS as the internal standard and reported with the following symbols (the same applicable to the following examples).

s:Singlet
d:Doublet
m:Multiplet
b:Broad line (1) IR (film method): $\nu_{max}$; 3300, 2950, 1480, 1270, 1140 $cm^{-1}$.

(2) NMR (CDCl$_3$, ppm):δ; 1.43–3.00 (m, 7H), 3.43 (bs, 1H), 4.13 (d, 2H, J=7 Hz), 7.27 (s, 4H), 7.67 (s, 1H), 7.80 (s, 1H).

EXAMPLE 2

Production of 1-(4-chlorobenzyl)-2-(1H-1,2,4-triazol-1-ylmethyl)cyclopentan-1-ol (Compound No. 2 of Table 1)

In a solution of 3.8680 g of 4-chlorobenzyl chloride in 25.1 ml of anhydrous diethyl ether, 0.555 g of magnesium powder and a catalytic amount of iodine were added and stirred at room temperature until generation of foam ceased. The resultant solution, after adding dropwise a solution of 2.5130 g of 2-(1H-1,2,4-triazol-1-ylmethyl)-cyclopentanone in 12.6 ml of anhydrous diethyl ether, was stirred at room temperature for 30 minutes.

The reaction mixture consequently obtained was added with 1N HCl and extracted with chloroform to obtain an organic layer. This organic layer was washed with water, dried over anhydrous sodium sulfate, and evaporated under a reduced pressure.

The residue of the evaporation was purified by silica gel column chromatography (eluate - ethyl acetate), to obtain 1.1079 g of a compound No. 2.

This compound No. 2 was found to possess the following properties.

(1) Melting point:127° to 130° C.
(2) IR (KBr method): $v_{max}$; 3300, 2950, 2910, 1520, 1490, 1420, 1280, 1140, 1090, 1010, 500 cm$^{-1}$.
(3) NMR (CDCl$_3$, ppm):δ: 1.10–2.00 (m, 7H), 2.23 (s, 1H, OH), 2.58 (s, 2H), 4.14 (dd, 1H, J=14.0 Hz, 6.6 Hz), 4.48 (dd, 1H, J=14.0 Hz, 6.6 Hz), 7.03–7.50 (m, 4H), 7.98 (s, 1H), 8.13 (s, 1H).

EXAMPLE 3

Production of 1-(4-chlorobenzyl)-2-(1H-imidazol-1-ylmethyl)-cyclopentan-1-ol (Compound No. 3 of Table 1)

In a solution of 6.0597 g of 4-chlorobenzyl chloride in 19.6 ml of anhydrous diethyl ether, 0.8530 g of magnesium powder and a catalytic amount of iodine were added and stirred at room temperature until generation of foam ceased. The resultant solution, after adding dropwise a solution of 1.9568 g of 2-(1H-imidazol-1-ylmethyl)cyclopentanone in 9.8 ml of anydrous diethyl ether, was stirred at room temperature for 30 minutes.

The resultant reaction mixture was added with 1N HCl and extracted with chloroform to obtain an organic layer. This organic layer was washed with water, dried over anhydrous sodium sulfate, and evaporated under a reduced pressure.

The residue of the evaporation was purified by silica gel column chromatography (eluate - 15:1 mixture of chloroform and methanol) to obtain 1.5027 g of a compound No. 3, and which was recrystallized from ethyl acetate to afford 1.2059 g of pure compound No. 3.

This compound was found to possess the following properties.

(1) Melting point:152° to 153° C.
(2) IR (KBr method): $v_{max}$; 3125, 2950, 1490, 1230, 1110, 1090, 1080, 730, 660 cm$^{-1}$.
(3) NMR (CDCl$_3$, ppm):δ; 1.27–2.17 (m, 7H), 2.27 (s, 1H, OH), 2.63 (s, 2H), 3.85 (dd, 1H, J=14.0 Hz, 6.6 Hz), 4.20 (dd, 1H, J=14.0 Hz, 6.6 Hz), 6.93 (d, 1H, J=1.6 Hz), 7.03 (d-like, 1H), 7.13–7.43 (m, 4H), 7.47 (bs, 1H).

EXAMPLE 4

Production of 2-(1H-imidazol-1-ylmethyl)cyclopentanone ethyleneketal (IV)

After washing 1.0319 g of 60% NaH with anhydrous benzene, 23.7 ml of anhydrous dimethyl formamide was added thereto. Subsequently after mixed with 1.7563 g of imidazole, the mixture was stirred at room temperature until generation of foam ceased. The resultant reaction mixture was added dropwise with a solution of 4.7357 g of 2-methanesulfonyloxymethylcyclopentanone ethyleneketal (VII) in 9.5 ml of anhydrous dimethyl formamide at room temperature, and stirred over an oil bath at 90° C. for 1 hour to complete the reaction. The reaction solution was poured into ice water and extracted with methylene chloride, to obtain an organic layer. This organic layer was washed with water, dried over anhydrous sodium sulfate, and evaporated under a reduced pressure.

The residue of the evaporation was purified by silica gel column chromatography (eluate - ethyl acetate), to obtain 3.6593 g of an oily compound indicated in the caption.

This compound was found to possess the following properties.

(1) IR (film method): $v_{max}$; 2960, 2880, 1510, 1230, 1025, 665 cm$^{-1}$.
(2) NMR (CDCl$_3$, ppm)$v$; 1.05–2.05 (m, 6H), 2.05–2.75 (m, 1H), 3.81 (dd, 1H, J=14.0 Hz, 6.2 Hz), 3.83 (d-like, 4H, J=1.4 Hz), 4.15 (dd, 1H, J=14.0 Hz, 6.2 Hz), 6.94 (d-like, 1H), 7.04 (s-like, 1H), 7.48(bs, 1H).

EXAMPLE 5

Production of 2-(1H-1,2,4-triazol-1-ylmethyl)cyclopentanone ethyleneketal (IV)

After washing 0.6475 g of 60% NaH with anhydrous benzene, 14.9 ml of anhydrous dimethyl formamide was added thereto. Subsequently after mixed with 1.1181 g of 1,2,4-triazole, the mixture was stirred at room temperature until generation of foam ceased. Into the resultant reaction mixture, solution of 2.9715 g of 2-methanesulfonyloxymethylcyclopentanone ethyleneketal (VII) in 6.0 ml of anhydrous dimethyl formamide were added at room temperature, and stirred over an oil bath at 90° C. for 1 hour to complete the reaction. The reaction solution was poured into ice water and extracted with methylene chloride to obtain an organic layer. This organic layer was washed with water, dried over anhydrous sodium sulfate, and evaporated under a reduced pressure.

The residue of the evaporation was purified by silica gel column chromatography (eluate - ethyl acetate), to obtain 2.1972 g of an oily compound indicated in the caption.

The compound was found to possess the following properties.

(1) IR (film method): $v_{max}$; 2960, 2880, 1510, 1280, 1210, 1140, 1025, 680 cm$^{-1}$.
(2) NMR (CDCl$_3$, ppm): $v$; 1.13–2.13 (m, 6H), 2.29–2.82 (m, 1H), 3.49–3.96 (m, 4H), 3.98 (dd, 1H, J=13.6 Hz, J=6.2 Hz), 4.31 (dd, 1H, J=13.6 Hz, J=6.2 Hz), 7.79 (s, 1H), 7.99 (s, 1H).

EXAMPLE 6

Production of 2-(1H-imidazol-1-ylmethyl)cyclopentanone (II)

In an oil bath, 3.5603 g of 2-(1H-imidazol-1-ylmethyl)cyclopentanone ethyleneketal (IV) and 17.8 ml of 2N hydrochloric acid added thereto were stirred at 60° C. for 5 hours. The resultant reaction solution was left cooling. Then, it was neutralized with an aqueous 1N potassium hydroxide solution and extracted with methylene chloride, to obtain an organic layer. This organic layer was washed with water, dried over anhydrous sodium sulfate, and evaporated under a reduced pressure.

The residue of the evaporation was purified by silica gel column chromatography (eluate - ethyl acetate), to obtain 2.5451 g of an oily compound indicated in the caption.

This compound was found to possess the following properties.

(1) Refractive index:1.4947 (22.0° C.).
(2) IR (film method): $\nu_{max}$; 2970, 1740, 1500, 1240, 1160, 1080 $cm^{-1}$.
(3) NMR ($CDCl_3$, ppm):δ; 1.07–2.73 (m, 7H), 4.07 (s-like, 1H), 4.15 (s-like, 1H), 6.78 (d, 1H, J=1.6 Hz), 6.92 (s-like, 1H), 7.33 (bs, 1H).

EXAMPLE 7

Production of 2-(1H-1,2,4-triazol-1-ylmethyl)-cyclopentanone (II)

After washing 0.9417 g of 60% NaH with anhydrous benzene, 18.9 ml of anhydrous dimethyl formamide was added thereto. The mixture and 1.6262 g of 1,2,4-triazole added thereto were stirred at room temperature until generation of foam subsided. The resultant mixture and a solution of 3.7715 g of 2-methanesulfonyloxymethylcyclopentanone (V) in 7.5 ml of anhydrous dimethyl formamide added dropwise thereto at room temperature were stirred at room temperature for 30 minutes. The reaction solution consequently formed was poured into ice water and extracted with methylene chloride to obtain an organic layer. This organic layer was washed with water, dried over anhydrous sodium sulfate, and evaporated under a reduced pressure. The residue of the evaporation was purified by silica gel column chromatography (eluate - ethyl acetate) to obtain 2.6254 g of an oily compound indicated in the caption.

This compound was found to possess the following properties.

(1) Refractive index:1.4922 (22.5° C.).
(2) IR (film method): $\nu_{max}$, 1740, 1510, 1280, 1140 $cm^{-1}$.
(3) NMR ($CDCl_3$, ppm):ν; 1.11–3.01 (m, 7H), 4.20 (dd, 1H, J=14.0 Hz, J=5.0 Hz), 4.50 (dd, 1H, J=14.0 Hz, J=5.6 Hz), 7.84 (s, 1H), 8.02 (s, 1H).

Now, examples for demonstrating the effectiveness of the compounds of this invention will be cited. The carrier, the diluent, and the adjuvants, the mixing ratio thereof, and the contents of the active ingredient can be varied in wide ranges.

EXAMPLE 8

(Dust)

A composition was prepared by pulverizing and mixing the following components in the indicated proportions.

| | |
|---|---|
| Compound of the present invention (Compound No. 2) | 3 parts by weight |
| Clay | 40 parts by weight |
| Talc | 57 parts by weight |

The composition was used as a dust agent.

EXAMPLE 9

(Wettable powder)

A composition was prepared by pulverizing and mixing the following components.

| | |
|---|---|
| Compound of the present invention (Compound No. 3) | 50 parts by weight |
| Lignin sulfonate | 5 parts by weight |
| Alkylsulfonate | 3 parts by weight |
| Diatomaceous earth | 42 parts by weight |

The composition was diluted suitably with water prior to actual use.

EXAMPLE 10

(Granules)

A composition was prepared by uniformly mixing the following components, kneading the resultant mixture with water, molded in a granular form with an extrusion pelletizer, and dried to produce granules.

| | |
|---|---|
| Compound of the present invention (Compound No. 1) | 5 parts by weight |
| Bentonite | 43 parts by weight |
| Clay | 45 parts by weight |
| Lignin sulfonate | 7 parts by weight |

EXAMPLE 11

(Emulsion)

An emulsion was prepared by uniformly mixing and emulsifying the following components in the indicated proportions.

| | |
|---|---|
| Compound of the present invention (Compound No. 7) | 30 parts by weight |
| Polyoxyethylene alkylallyl ether | 10 parts by weight |
| Polyoxyethylene sorbitan monolaurate | 3 parts by weight |
| Xylene | 57 parts by weight |

EXAMPLE 12

(Test for control of Pseudoperonospora cubensis of cucumber)

Cucumbers (species Sagami Hampaku) were grown in earthen pots 10 cm in diameter (one plant per pot and three pots per plot of treatment) to the two-leaf stage. A wettable powder prepared as described in Example 8 was suspended in water in an active ingredient concentration of 500 ppm. This suspension was applied to the cucumber leaves at a rate of 5 ml per pot. The wet leaves were air dried. Then, a suspension of spores of *Pseudoperonospora cubensis* of cucumber collected from disease cucumber leaves was inoculated to the dry cucumber leaves by spraying. The treated leaves were left standing in a humid atmosphere at 20° to 22° C. for 24 hours. After this standing, the cucumbers were left standing in a greenhouse. On the 5th to 7th day after the inoculation, the treated cucumber leaves were examined to determine the degree of infection on the following scale of evaluation. The control index of the fungicide was calculated from the following formula.

| (Scale of evaluation) | |
|---|---|
| Degree of infection | Degree of disease |
| 0 | Not infected |
| 0.5 | Less than 10% of infected area ratio |
| 1 | Not less than 10% and less than 20% of infected area ratio |
| 2 | Not less than 20% and less than 40% of infected area ratio |
| 3 | Not less than 40% and less than 60% of infected area ratio |
| 4 | Not less than 60% and less than 80% of infected area ratio |
| 5 | Not less than 80% of infected area ratio |

$$\text{Control index (\%)} = \left(1 - \frac{\text{Degree of infection in treated plot}}{\text{Degree of infection in control plot}}\right) \times 100$$

The results of the test are shown in Table 2.

TABLE 2

| Compound No. | Concentration (ppm) | Control index (%) |
|---|---|---|
| 1 | 500 | 0 |
| 2 | 500 | 0 |
| 3 | 500 | 10 |
| 4 | 500 | 85 |
| 5 | 500 | 80 |
| 7 | 500 | 0 |

EXAMPLE 13

(Test for control of *Puccinia recondita* of wheat)

Young wheat seedling (species Norin No. 64) were grown in earthen pots 10 cm in diameter (16 plants per pot) to the two-leaf stage. A wettable powder prepared as described in Example 8 was suspended in water in an active ingredient concentration of 500 ppm. This suspension was applied to the wheat seedling at a rate of 5 ml per pot. The wheat leaves wet with the suspension were air dried. Then, a suspension of spores of *Puccinia recondita* collected from disease wheat leaves was inoculated to the dry wheat leaves by spraying. The treated wheat leaves were left standing in a humid atmosphere at 20° to 23° C. for 24 hours. After this standing, the wheat plants were left standing in a greenhouse of glass. On the 7th to 10th day after the inoculation, the treated wheat leaves of 10 plants were examined to determine the degree of infection on the following scale of evaluation. The control index of the fungicide was calculated from the following formula using the average degree of infection per leaf.

| (Scale of evaluation) | |
|---|---|
| Degree of infection | Degree of disease |
| 0 | Not infected |
| 0.5 | Less than 10% of infected area ratio |
| 1 | Not less than 10% and less than 20% of infected area ratio |
| 2 | Not less than 20% and less than 40% of infected area ratio |
| 3 | Not less than 40% and less than 60% of infected area ratio |
| 4 | Not less than 60% and less than 80% of infected area ratio |
| 5 | Not less than 80% of infected area ratio |

$$\text{Control index (\%)} = \left(1 - \frac{\text{Degree of infection in treated plot}}{\text{Degree of infection in control plot}}\right) \times 100$$

The results of the test are shown in Table 3.

TABLE 3

| Compound No. | Concentration (ppm) | Control index (%) |
|---|---|---|
| 1 | 500 | 80 |
| 2 | 500 | 100 |
| 3 | 500 | 85 |
| 4 | 500 | 60 |
| 5 | 500 | 60 |
| 7 | 500 | 80 |

EXAMPLE 14

(Test for control of *Erysiphe graminis* f. sp. *tritici* of wheat)

Young wheat seedlings (species Norin No. 64) were grown in earthen pots 10 cm in diameter (16 plants per pot and 3 pots per plot of treatment) to the two-leaf stage. A wettable powder prepared as described in Example 8 was suspended in water in an active ingredient concentration of 500 ppm. This suspension was applied to the wheat seedlings at a rate of 5 ml per pot. The wheat leaves wet with the suspension were air dried. Then, a suspension of spores of *Erysiphe graminis* f. sp. *tritici* collected from disease wheat leaves was inoculated to the dry wheat leaves by spraying. The treated wheat leaves were left standing in a humid atmosphere at 20° to 24° C. for 24 hours. After this standing, the wheat plants were left standing in a greenhouse. On the 9th to 11th day after the inoculation, the treated wheat leaves were examined to determine the degree of infection on the following scale of evaluation. The control index of the fungicide was calculated from the following formula.

| (Scale of evaluation) | |
|---|---|
| Degree of infection | Degree of disease |
| 0 | Not infected |
| 0.5 | Less than 10% of infected area ratio |
| 1 | Not less than 10% and less than 20% of infected area ratio |
| 2 | Not less than 20% and less than 40% of infected area ratio |
| 3 | Not less than 40% and less than 60% of infected area ratio |
| 4 | Not less than 60% and less than |

-continued

| (Scale of evaluation) | |
|---|---|
| Degree of infection | Degree of disease |
| 5 | 80% of infected area ratio Not less than 80% of infected area ratio |

$$\text{Control index (\%)} = \left(1 - \frac{\text{Degree of infection in treated plot}}{\text{Degree of infection in control plot}}\right) \times 100$$

The results of the test are shown in Table 4.

TABLE 4

| Compound No. | Concentration (ppm) | Control index (%) |
|---|---|---|
| 1 | 500 | 100 |
| 2 | 500 | 100 |
| 3 | 500 | 95 |
| 4 | 500 | 80 |
| 5 | 500 | 95 |
| 7 | 500 | 100 |

EXAMPLE 15 diameter of colony. The rate of inhibiting hypha growth of the compound was determined by comparing the growth of germ in the plot of treatment with that in the control plot and by the calculation based on the following formula using the result of comparison.

$$R\ (\%) = (dc - dt) \cdot 100/dc$$

wherein R is the rate of inhibiting hypha growth (%), dc is the diameter of colony on the untreated plate, and dt is the diameter of colony on the treated plate.

The results were evaluated on the following 5-point scale. They are shown in Table 5.

| (Degree of inhibiting growth) | |
|---|---|
| 5 | not less than 90% of the rate of inhibiting hypha growth |
| 4 | not less than 71% and less than 90% of the rate of inhibiting hypha growth |
| 3 | not less than 41% and less than 71% of the rate of inhibiting hypha growth |
| 2 | not less than 21% and less than 41% of the rate of inhibiting hypha growth |
| 1 | less than 21% of the rate of inhibiting hypha growth |

TABLE 5

| Compound No. | Concentration of compound (μg/ml) | Disease germ used | | | | | | | | | | | | | | |
|---|---|---|---|---|---|---|---|---|---|---|---|---|---|---|---|---|
| | | P.o. | C.m. | G.f. | H.s. | R.s. | Bo.c. | S.s. | F.n. | F.c. | F.r. | C.l. | C.b. | S.c. | V.m. | A.k. | A.m. |
| 1 | 100 | 4 | 4 | 5 | 3 | 2 | 5 | 5 | 5 | 5 | 5 | 3 | 4 | 5 | 5 | 3 | 3 |
| 2 | 100 | 5 | 5 | 5 | 4 | 3 | 5 | 5 | 5 | 5 | 5 | 4 | 5 | 5 | 5 | 4 | 3 |
| 3 | 100 | 5 | 5 | 5 | 4 | 3 | 3 | 5 | 5 | 5 | 5 | 4 | 4 | 5 | 5 | 3 | 4 |
| 4 | 100 | 5 | 5 | 5 | 5 | 3 | 5 | 5 | 5 | 5 | 5 | 5 | 5 | 5 | 5 | 4 | 4 |
| 5 | 100 | 5 | 5 | 3 | 4 | 3 | 5 | 5 | 3 | 3 | 3 | 3 | 3 | 5 | 5 | 3 | 3 |
| 6 | 100 | 5 | 5 | 5 | 4 | 3 | 3 | 5 | 5 | 5 | 5 | 4 | 4 | 5 | 5 | 3 | 4 |
| 7 | 100 | 5 | 4 | 3 | 3 | 3 | 4 | 5 | 3 | 3 | 3 | 3 | 4 | 5 | 5 | 2 | 3 |

The acronyms used in the table indicate the following germs.
P.o.: *Pyricularia oryzae* on rice plant
F.c.: *Fusarium oxysporum f.cucumerinum* on cucumber
C.m.: *Cochliobolus miyabeanus* on rice plant
F.r.: *Fusarium oxysporum f.raphani* on Japanese radish
G.f.: *Gibberella fujikuroi* on rice plant
C.l.: *Colletotrichum lagenarium* on melons
H.s.: *Helminthosporium sigmoideum* on rice
C.b.: *Cercospola beticola* on sugar beet
R.s.: *Rhizoctonia solani* on rice plant
S.c.: *Sclerotinia cinerea* on peach
Bo.c.: *Botrytis cinerea*
V.m.: *Valsa mali* on apple
S.s.: *Sclerotinia sclerotirum*
A.m.: *Alternaria mali* on apple
F.n.: *Fusarium oxysporum f.niveum* on water melon
A.k.: *Alternaria alternata (kikuchiana)* on pear (Test for fungicidal ability against various disease germs)

Various azole derivatives according to the present invention were tested for fungicidal ability against various disease germs as follows. Method of test:

Various compounds of the present invention was dissolved in dimethyl sulfoxide in a prescribed concentration. In an Erlenmeyer flask having an inner volume of 100 ml, 0.6 ml of the resultant solution and 60 ml of a PSA culture medium of about 60° C. were thoroughly mixed. The resultant mixture was poured into a petri dish and left solidifying therein. A plate culture medium in which a test germ had been cultured was punched out by a cork borer 4 mm in diameter. A disc of plate culture medium was superposed by way of inoculation on a plate containing the aforementioned solution. The germ was incubated at the optimum growth temperature thereof for one to three days after the inoculation. The growth of germ was determined by measuring the

What is claimed is:
1. An azole derivative represented by the formula (I):

wherein X and Y independently represent a halogen atom, a phenyl group or a hydrogen atom, providing that at least one of X and Y is not a hydrogen atom, n represents an integer of 0, 1 or 2, and A represents a nitrogen atom.

2. An agricultural/horticultural fungicide comprising as an active ingredient a fungicidally effective amount of an azole derivative represented by the formula (I):

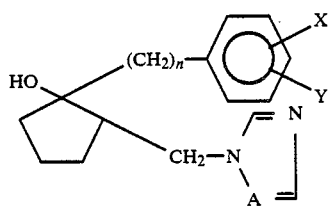

wherein X and Y independently represent a halogen atom, a phenyl group or a hydrogen atom, providing that at least one of X and Y is not a hydrogen atom, n represents an integer of 0, 1 or 2, and A represents a nitrogen atom.

3. A method for preventing and curing plant diseases which comprises applying a fungicidally effective amount of an azole derivative represented by the following formula (I):

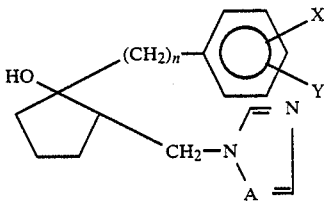

wherein A, X, Y and n have the same meanings as defined in claim 1, to plants.

* * * * *